United States Patent [19]

Cagen

[11] 4,451,482

[45] May 29, 1984

[54] METHOD OF PREVENTING OR AMELIORATING PYRETHROID SKIN SENSORY STIMULATION

[75] Inventor: Stuart Z. Cagen, Houston, Tex.

[73] Assignee: Shell Oil Company, Houston, Tex.

[21] Appl. No.: 371,023

[22] Filed: Apr. 22, 1982

[51] Int. Cl.$^3$ .................... A01N 43/16; A61K 31/355
[52] U.S. Cl. .................................................. 424/284
[58] Field of Search ........................................ 424/284

[56] References Cited

U.S. PATENT DOCUMENTS

| | | | |
|---|---|---|---|
| 3,943,248 | 3/1976 | Shulman | 424/196 |
| 4,144,325 | 3/1979 | Voyt | 424/284 |
| 4,154,823 | 5/1979 | Schutt | 424/284 |
| 4,181,725 | 1/1980 | Voorhees et al. | 424/258 |
| 4,325,965 | 4/1982 | Chiba | 424/284 |

FOREIGN PATENT DOCUMENTS 48-14932  5/1973  Japan.
1553805  10/1979  United Kingdom.

OTHER PUBLICATIONS

Basic Clin. Nutr. (1980), 1 (Vitam. E. Compr. Treatise) pp. 474–494–Menyel.

*Primary Examiner*—Douglas W. Robinson

[57] ABSTRACT

Pyrethroid skin sensory stimulation is prevented or ameliorated by applying to the skin of a human or animal a composition comprising α-tocopherol or ester thereof optionally in association with a pharmaceutical carrier.

11 Claims, No Drawings

METHOD OF PREVENTING OR AMELIORATING PYRETHROID SKIN SENSORY STIMULATION

BACKGROUND OF THE INVENTION

1. Field of the Invention

The present invention relates to a method of preventing or ameliorating pyrethroid skin sensory stimulation.

2. Description of the Prior Art

Pyrethroids and formulations thereof, including various 3-phenoxybenzyl esters and α-cyano-3-phenoxybenzyl esters, such as fenvalerate (α-cyano-3-phenoxybenzyl α-isopropyl-p-chlorophenylacetate), α-cyano-3-phenoxybenzyl α-isopropyl-p-(difluoromethoxy)phenylacetate and cypermethrin (α-cyano-3-phenoxybenzyl 2,2-dimethyl-3-(2,2-dichlorovinyl)cyclopropanecarboxylate, are known to cause undesirable skin sensory stimulation. This skin sensory stimulation is not accompanied by visible effects to the skin but is characterized by such symptoms (which may vary over time and with the individual) as stinging, itching, burning, numbness and the like. These symptoms usually last for only a few hours or days but are annoying to the individuals affected from their contact with pyrethroids. The more prolonged effects are associated with enhanced sensitivity to other stimuli, e.g. chemical irritants or physical sensations. Recommended procedures to wash with soap and water do not prevent or successfully ameliorate the skin sensory stimulation. Other ameliorating or prophylactic materials, including some over-the-counter anti-itch-claiming pharmaceuticals, usually do not protect, or successfully ameliorate and sometimes even make the sensation worse or are not medically or practically feasible.

SUMMARY OF THE INVENTION

The present invention is directed to a method of preventing or ameliorating pyrethroid skin sensory stimulation and associated enhanced sensitivity to other stimulation which comprises applying to the skin of a human or an animal a composition comprising as its active component α-tocopherol or an ester thereof optionally in association with a pharmaceutically-acceptable carrier.

The effective agent used in the present invention is selected from α-tocopherol or, preferably, a pharmaceutically-acceptable ester thereof, for example, the acetic acid ester, the succinic acid ester and the like. According to the present invention, α-tocopherol or any ester thereof or mixtures of at least two or more of the above can be used. α-Tocopherol in this invention includes the natural single isomer or a synthetic isomer form or racemic mixture or other form, such as Vitamin E. Vitamin E is mainly found in plant materials as α-tocopherol, and then is usually accompanied by β-tocopherol and γ-tocopherol. The preferred source of α-tocopherol for extraction are vegetable oils, such as seed germ oils, alfalfa and lettuce. α-Tocopherol or Vitamin E is preferably used in the ester form, e.g. acetate, to avoid any side responses of the skin which some subjects might experience to the use of α-tocopherol or Vitamin E.

The α-tocopherol compositions are applied in the method of the invention topically. To prevent pyrethroid skin sensory stimulation it is desirable to apply the composition to the skin prior to possible exposure to a pyrethroid or pyrethroid composition. In this manner, the α-tocopherol composition seems to function like a prophylactic and prevents pyrethroid skin stimulation. In the event that the skin is unexpectedly and mildly exposed to a pyrethroid or pyrethroid composition, application of the α-tocopherol composition to the exposed skin immediately or within a few hours, e.g. about two to about four hours or more after exposure will usually prevent or ameliorate the pyrethroid skin sensory stimulation. When the unexpected exposure is of such intensity or because of time elapsed after exposure that the skin sensory stimulation has begun, application of the α-tocopherol composition to the site of skin which is subject to the skin sensory stimulation will eliminate or reduce the skin sensory stimulation.

Since the skin sensory stimulation effect of pyrethroids does not produce any visible sign, change or break in the skin, any pharmaceutically-acceptable carrier which can be applied directly to the skin surface is suitable for use in preparing the α-tocopherol compositions of the invention. For example, the active ingredient can be dissolved in a liquid, dispersed or emulsified in a medium in a conventional manner to form a liquid preparation or is mixed with a solid carrier to form a paste, ointment or cream. If desired, an emulsifier, dispersing agent, wetting agent, odor-modifying agent, stabilizer or propellant can be added to the composition.

When used, the carrier can have an aqueous or oil base and, as such, can be a cream, vegetable oil, animal oil or wax. Preferably, the carrier is a vegetable oil, for example, coconut oil, olive oil, peanut oil, castor oil, sesame oil, corn oil, linseed oil, cottonseed oil, wheat germ oil, soybean oil, sunflower oil and the like. Particularly useful carriers for the invention are soybean oil, sesame oil, sunflower oil, corn oil, cottonseed oil, wheat germ oil or a mixture of two or more thereof. Corn oil is especially useful. Prevention or amelioration can be obtained with use of vegetable oil compositions of α-tocopherol in exposures where the pyrethroid is in a formulated or technical-grade form.

The effective dosage of the α-tocopherol composition used in the present invention is not critically limited, but can be variable depending on the amount of exposure, the time before or after exposure of the application and the sensitivity of the subject human or animal. When used in the preferred method as a pre-exposure prophylactic, all the skin expected to be exposed to a pyrethroid or pyrethroid formulation should be completely covered with the composition, that is, the unstimulated skin is covered. In general, one application per exposure or one application per day of expected exposure is usually adequate. The effective dose of the active ingredient, α-tocopherol, or, more preferably, an ester thereof, when formulated can vary widely. The dosage composition can vary depending on the condition (sensitivity) of the subject, human or animal. A useful method of the invention comprises applying about 5% to about 100% by weight α-tocopherol or Vitamin E, or preferably the acetate thereof, containing composition in a carrier of mixed vegetable oils or corn oil. Preferably, the α-tocopherol or Vitamin E or, more preferably, the acetate thereof, is present in about 20% to about 40% by weight of the composition.

A composition of α-tocopherol or an ester thereof optionally in a pharmaceutical carrier was effective in preventing or ameliorating pyrethroid skin sensory stimulation in tests conducted on the bare skin of guinea pigs and humans. For example, a composition of 5%, 20%, 50%, or 100% Vitamin E, or acetate ester in corn oil or alcohol, and a composition of 40% Vitamin E acetate in a mixture of corn oil, wheat germ oil, safflower oil and sesame oil, each was effective in preventing or ameliorating pyrethroid skin sensory stimulation when applied pre-exposure or post-exposure to fenvalerate or a formulation thereof as the pyrethroid. When specifically evaluated, these treatments also eliminated the pyrethroid associated, enhanced sensitivity to other stimuli.

I claim:

1. A method of preventing or ameliorating pyrethroid skin sensory stimulation and associated enhanced sensitivity to other stimulation which comprises applying to the skin of a human or an animal a composition comprising an effective amount of α-tocopherol or ester thereof optionally in a pharmaceutically-acceptable carrier.

2. A method according to claim 1 wherein the active component is in a pharmaceutically-acceptable carrier.

3. A method according to claim 2 wherein the carrier is vegetable oil or animal oil.

4. A method according to claim 3 wherein the carrier is a vegetable oil.

5. A method according to claim 4 wherein the vegetable oil is selected from soybean oil, sesame oil, sunflower oil, corn oil, cottonseed oil, wheat germ oil or a mixture thereof.

6. A method according to claim 5 wherein the vegetable oil is corn oil.

7. A method according to claim 2 wherein α-tocopherol, α-tocopheryl acetate or α-tocopheryl succinate is the active component.

8. A method according to claim 7 wherein α-tocopherol is the active component.

9. A method according to claim 2 wherein Vitamin E acetate is the active component.

10. A method according to claim 2 wherein the active component is present in the amount of about 5% to about 100% by weight of the composition.

11. A method according to claim 10 wherein the active component is present in the amount of about 20% to about 40% by weight of the composition.

* * * * *